US009480405B2

United States Patent
Oki et al.

(10) Patent No.: US 9,480,405 B2
(45) Date of Patent: Nov. 1, 2016

(54) PHOTODYNAMIC DIAGNOSIS APPARATUS, PHOTODYNAMIC DIAGNOSIS METHOD AND DEVICE

(71) Applicant: Sony Corporation, Tokyo (JP)

(72) Inventors: Tomoyuki Oki, Kanagawa (JP); Shiho Hakomori, Kanagawa (JP); Koshi Tamamura, Tokyo (JP); Takao Miyajima, Kanagawa (JP)

(73) Assignee: Sony Corporation, Tokyo (JP)

( * ) Notice: Subject to any disclaimer, the term of this patent is extended or adjusted under 35 U.S.C. 154(b) by 303 days.

(21) Appl. No.: 13/933,825

(22) Filed: Jul. 2, 2013

(65) Prior Publication Data

US 2014/0031699 A1    Jan. 30, 2014

(30) Foreign Application Priority Data

Jul. 26, 2012  (JP) .................................. 2012-165403

(51) Int. Cl.
| | | |
|---|---|---|
| *A61B 6/00* | (2006.01) | |
| *A61B 5/00* | (2006.01) | |
| *G01N 21/64* | (2006.01) | |
| *A61B 1/04* | (2006.01) | |

(52) U.S. Cl.
CPC ........... *A61B 5/0071* (2013.01); *A61B 5/0084* (2013.01); *G01N 21/6408* (2013.01); *G01N 21/6456* (2013.01); *A61B 1/043* (2013.01); *A61B 5/7242* (2013.01); *G01N 2021/6484* (2013.01)

(58) Field of Classification Search
CPC .. A61B 1/043; A61B 1/0638; A61B 5/0071; A61B 1/00186; A61B 5/0084; A61B 5/7242; G01N 21/6456; G01N 21/6408; G01N 2021/6484
USPC ................................................ 600/473–480
See application file for complete search history.

(56) References Cited

U.S. PATENT DOCUMENTS

| | | | | |
|---|---|---|---|---|
| 5,318,023 A | * | 6/1994 | Vari ..................... | A61B 5/0059 128/898 |
| 5,817,025 A | * | 10/1998 | Alekseev .............. | G01J 3/4412 356/339 |
| 5,833,617 A | * | 11/1998 | Hayashi ............. | A61B 1/00009 250/461.1 |
| 6,002,137 A | * | 12/1999 | Hayashi ............. | A61B 1/00009 250/458.1 |
| 6,026,319 A | * | 2/2000 | Hayashi ............... | A61B 5/0071 600/476 |
| 6,280,378 B1 | * | 8/2001 | Kazuhiro ............. | A61B 1/0638 348/65 |
| 8,175,687 B2 | * | 5/2012 | Kang ................... | A61B 5/0071 600/473 |
| 2001/0055462 A1 | * | 12/2001 | Seibel ................ | A61B 1/00048 385/147 |
| 2002/0035330 A1 | * | 3/2002 | Cline ................. | A61B 1/00009 600/476 |
| 2005/0228231 A1 | * | 10/2005 | MacKinnon ............. | A61B 1/05 600/180 |
| 2005/0234302 A1 | * | 10/2005 | MacKinnon ....... | A61B 1/00186 600/181 |
| 2008/0239070 A1 | * | 10/2008 | Westwick .............. | A61B 1/045 348/68 |
| 2009/0095911 A1 | * | 4/2009 | Kim ................... | G01N 21/6408 250/363.01 |

(Continued)

FOREIGN PATENT DOCUMENTS

| | | |
|---|---|---|
| JP | 2008-043383 | 2/2008 |
| JP | 2011-218149 | 11/2011 |

OTHER PUBLICATIONS

Lazerphyrin 100mg for Injection, revised Apr. 2011. (13 pages).

*Primary Examiner* — Sanjay Cattungal
(74) *Attorney, Agent, or Firm* — K&L Gates LLP

(57) ABSTRACT

There is provided a photodynamic diagnosis apparatus including a light source for generating a light pulse having a time width shorter than a fluorescence lifetime of a photosensitizer, and a detector for measuring a time change waveform of the fluorescence to the light pulse.

15 Claims, 13 Drawing Sheets

(56) References Cited

U.S. PATENT DOCUMENTS

| | | | | |
|---|---|---|---|---|
| 2010/0145416 A1* | 6/2010 | Kang | ................... | A61B 5/0059 607/89 |
| 2010/0330611 A1* | 12/2010 | Mycek | ................ | A61B 5/0071 435/29 |
| 2011/0104056 A1* | 5/2011 | Hara | ................... | A61K 9/5153 424/1.65 |
| 2011/0313299 A1* | 12/2011 | Brennan, III | ........ | A61B 5/0086 600/478 |
| 2014/0163391 A1* | 6/2014 | Koizumi | ....................... | 600/476 |

\* cited by examiner

PHOTODYNAMIC DIAGNOSIS APPARATUS, PHOTODYNAMIC DIAGNOSIS METHOD AND DEVICE

CROSS REFERENCES TO RELATED APPLICATIONS

The present application claims priority to Japanese Priority Patent Application JP 2012-165403 filed in the Japan Patent Office on Jul. 26, 2012, the entire content of which is hereby incorporated by reference.

BACKGROUND

The present application relates to a photodynamic diagnosis apparatus, a photodynamic diagnosis method and a device usable therefor.

In general, as tumor cells are immature, porphyrin-based substances are easily bonded to lipoproteins in the cells, and porphyrin-based substances are slowly excreted from the cells to outside. By making full use of the characteristic and utilizing a difference between the excretion speeds of healthy cells and the tumor cells, when a porphyrin-based drug is intravenous injected, there can be provided a drug concentration difference between the healthy cells and the tumor cells. Thus, a tumor selected drug is born. Furthermore, by utilizing a photochemical action where a light energy is externally added to the drug and the drug is excited to provide fluorescence, the drug is developed into a photosensitizer for visualizing the drug concentration difference. Examples of the photosensitizer include Laserphyrin (see http://www.info.pmda.go.jp/go/pack/4299404D1028_1_05/). A diagnosis by a combination of the photosensitizer and a light is called as a photodynamic diagnosis, and has been utilized in a wide variety of clinical areas.

Photodynamic diagnosis apparatuses in the related art mainly sequentially irradiate a light from a laser or a lamp, measure fluorescence obtained by the photosensitizer, and determine tumors. However, according to the related art technology, there is no choice to determine the tumor cells only by a fluorescence intensity. In the photodynamic diagnosis, an improvement of an accuracy of tumor determination or an establishment of a diagnosis index other than information about the drug concentration read from the fluorescence intensity becomes one of important technologies. Japanese Patent Application Laid-open No. 2011-218149 and Japanese Patent Application Laid-open No. 2008-43383 relate to such technologies.

SUMMARY

In view of the above, it is desirable to provide a new and useful photodynamic diagnosis apparatus, a photodynamic diagnosis method and a device usable therefor.

It is also desirable to provide a photodynamic diagnosis apparatus being capable of improving an accuracy of tumor determination, a photodynamic diagnosis method and a device usable therefore.

It is still desirable to provide a photodynamic diagnosis apparatus being capable of establishing a new diagnosis index about the tumor staging and the invasion degree in the depth direction of the tumor, a photodynamic diagnosis method and a device usable therefore.

According to the present application, the photodynamic diagnosis apparatus includes a light source being capable of generating a light pulse shorter than a fluorescence lifetime of a photosensitizer, and a detector being capable of a time change waveform of the fluorescence to a light pulse (a fluorescence intensity is changed depending on a time).

According to the present application, a time change waveform of the fluorescence to the light pulse having a time width shorter than the fluorescence lifetime of the photosensitizer is measured. From the measurement results, tumors can be accurately determined. In addition, from the measurement results, a new diagnosis index about the tumor staging and the invasion degree in the depth direction of the tumor can be established.

The photodynamic diagnosis apparatus according to the present application may further include a controller for sequentially gaining the time change waveform of the fluorescence generated by the light pulse generated at the light source from the detector, integrating and averaging a plurality of the waveforms per repetition frequency, and gaining the fluorescence lifetime by subtracting a background signal from the waveform averaged.

According to the present application, as the time change waveform of fluorescence integrated per repetition frequency is used, the fluorescence lifetime can be easily calculated even if the fluorescence is faint.

According to the present application, the detector includes a device for measuring the time change waveform of the fluorescence to the light pulse at a response speed higher than the fluorescence lifetime of the photosensitizer. By using such a device, it is possible to accurately measure the time change waveform of the fluorescence. Examples of the device include a streak camera, a photomultiplier, a CCD, a CMOS and a photodiode.

The photodynamic diagnosis apparatus according to the present application may further include a driving unit for generating a synchronization signal that is synchronized with an electric pulse for driving the light source and an electric pulse for driving the detector and is delayed by the electric pulse. The light source generates the light pulse based on the electric pulse. The detector may control a light receiving duration of the fluorescence based on the synchronization signal. This allows the time change waveform of the fluorescence to be accurately measured with a simple configuration.

The photodynamic diagnosis apparatus according to the present application may further includes a dichroic mirror having high reflectance near a peak wavelength of the light pulse that reflects the light pulse from the light source, directs the light pulse to an object and transmits the fluorescence from the object, a long wavelength cut filter disposed at a light path between the light source and the dichroic mirror that blocks a wavelength longer than a peak wavelength of the light pulse, and a short wavelength cut filter disposed at a light path between the dichroic mirror and the detector that blocks a wavelength shorter than a peak wavelength of the photosensitizer. This allows the fluorescence lifetime be easily calculated even if the fluorescence is faint.

A photodynamic diagnosis method according to other embodiment of the present application includes generating a light pulse having a time width shorter than a fluorescence lifetime of a photosensitizer, irradiating an object with the light pulse generated, and measuring a time change waveform of fluorescence to the light pulse generated from the object.

According to the present application, a time change waveform of the fluorescence to the light pulse having a time width shorter than the fluorescence lifetime of the photosensitizer is measured. From the measurement results, tumors can be accurately determined. In addition, from the measurement results, a new diagnosis index about the tumor staging and the invasion degree in the depth direction of the tumor can be established. According to the present application, a fluorescence lifetime may be determined based on a time change waveform of fluorescence, and a diagnosis index about the tumor staging may be gained based on the fluorescence lifetime. According to the present application, a fluorescence lifetime may be determined based on a time change waveform of fluorescence, and a diagnosis index about an invasion degree of a tumor may be gained based on the fluorescence lifetime.

According to the present application, a time change waveform of the fluorescence generated by the light pulse may be sequentially gained, a plurality of the waveforms per repetition frequency may be integrated and averaged, and the fluorescence lifetime may be gained by subtracting a background signal from the waveform averaged. This allows the fluorescence lifetime be easily calculated even if the fluorescence is faint.

According to still other embodiment of the present application, a attachable/detachable device to a photodynamic diagnosis apparatus main body including a light source for generating a light pulse having a time width shorter than a fluorescence lifetime of a photosensitizer, and a detector for measuring a time change waveform of the fluorescence to the light pulse includes a cable for transmitting a light pulse generated by the light source, irradiating an object with the light pulse, inputting fluorescence to the light pulse irradiated, and transmitting the fluorescence to the detector, a dichroic mirror having high reflectance near a peak wavelength of the light pulse that reflects the light pulse from the light source, directs the light pulse to an object and transmits the fluorescence from the object, a long wavelength cut filter disposed at a light path between the light source and the dichroic mirror that blocks a wavelength longer than a peak wavelength of the light pulse, and a short wavelength cut filter disposed at a light path between the dichroic mirror and the detector that blocks a wavelength shorter than a peak wavelength of the photosensitizer. This allows the fluorescence lifetime be easily calculated even if the fluorescence is faint.

As described above, according to the present application, tumors can be accurately determined. In addition, according to the present application, a new diagnosis index about the tumor staging and the invasion degree in the depth direction of the tumor can be established.

These and other objects, features and advantages of the present application will become more apparent in light of the following detailed description of best mode embodiments thereof, as illustrated in the accompanying drawings.

Additional features and advantages are described herein, and will be apparent from the following Detailed Description and the figures.

DETAILED DESCRIPTION

Hereinafter, an embodiment of the present application will be described with reference to the drawings.

(Configuration of Photodynamic Diagnosis Apparatus)

Figure 1:
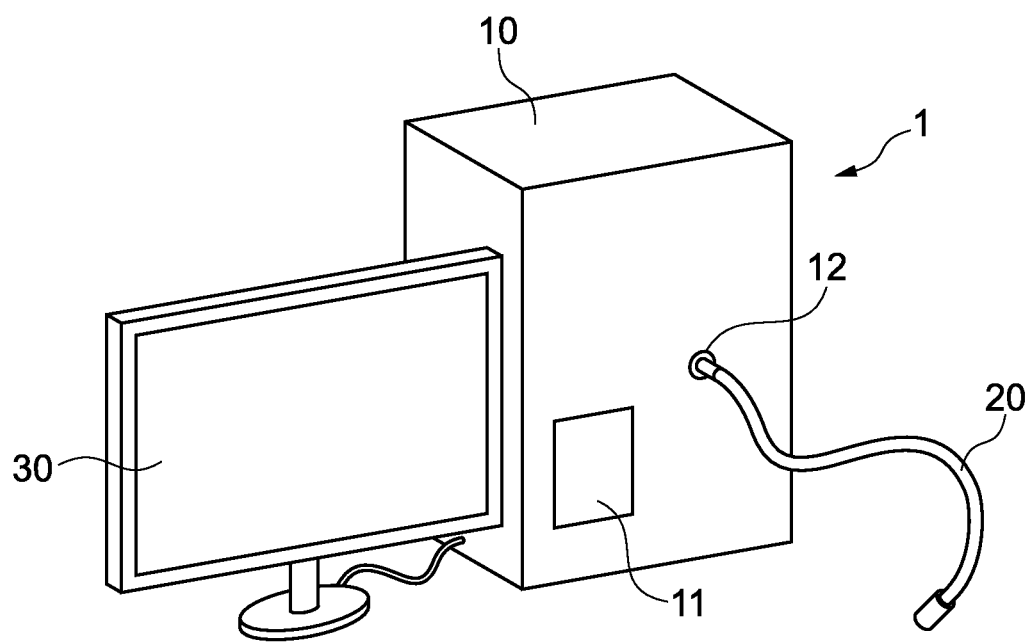
FIG. 1 is a perspective view showing an appearance of a photodynamic diagnosis apparatus according to an embodiment of the present application.

FIG. 1 is a perspective view showing an appearance of a photodynamic diagnosis apparatus according to an embodiment of the present application.

As shown in FIG. 1, the photodynamic diagnosis apparatus 1 includes a photodynamic diagnosis apparatus main body 10, a light transmission unit 20, and a monitor 30.

The photodynamic diagnosis apparatus main body 10 outputs a light pulse from a light input/output (I/O) unit 12 depending on an input operation by an operation unit 11. The light pulse outputted irradiate a sample (cells) 40 as an object via the light transmission unit 20 connected to the light I/O unit 12. Fluorescence generated from the sample 40 to the light pulse is inputted to the light I/O unit 12 via the light transmission unit 20.

Figure 2:
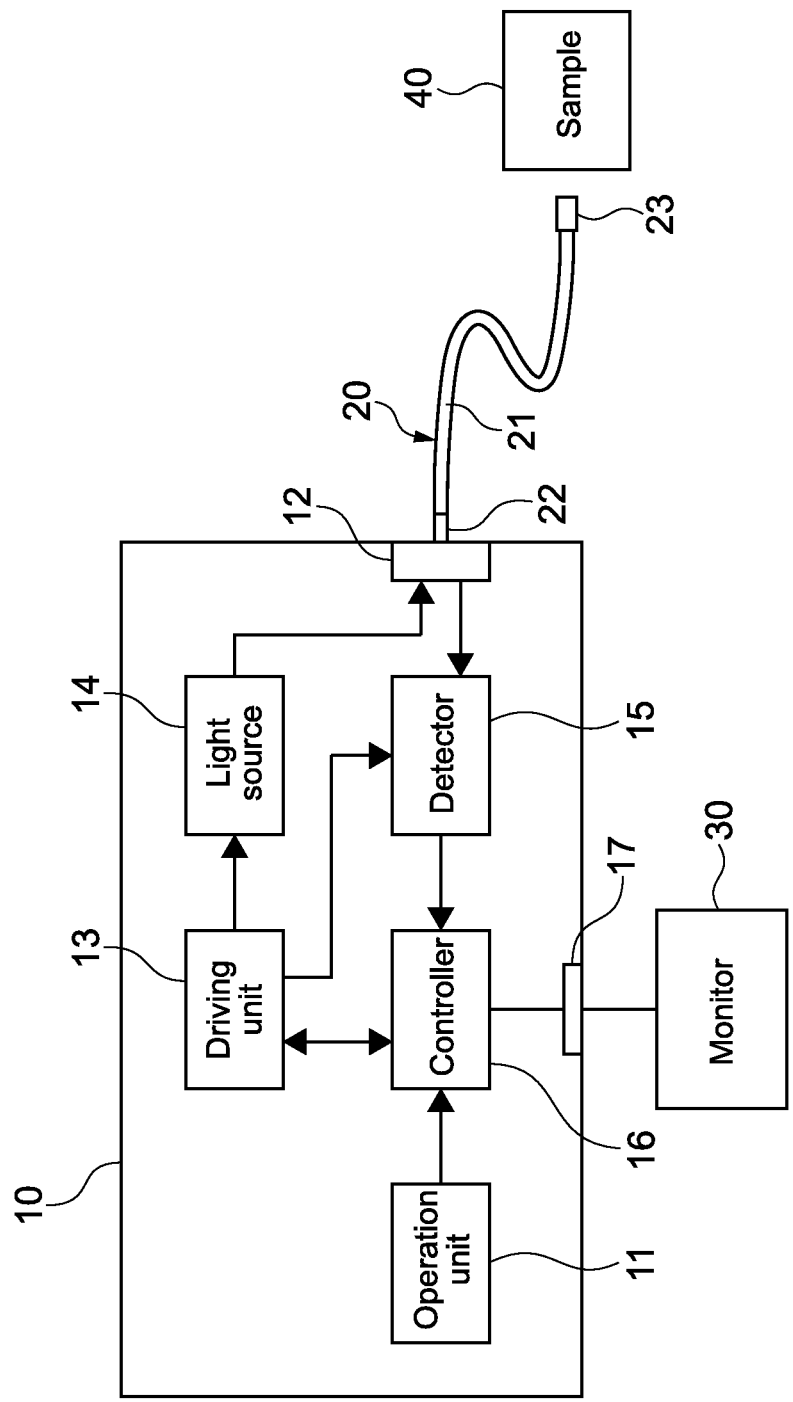
FIG. 2 is a block diagram showing a configuration of the photodynamic diagnosis apparatus shown in FIG. 1.

FIG. 2 is a block diagram showing a configuration of the photodynamic diagnosis apparatus 1.

As shown in FIG. 2, the photodynamic diagnosis apparatus main body 10 includes the operation unit 11, the light I/O unit 12, a driving unit 13, a light source 14, a detector 15, a controller 16 and a monitor connection unit 17.

An operator inputs operating instructions to the operation unit 11.

To the light I/O unit 12, the light transmission unit 20 is connected attachably/detachably. The light I/O unit 12 outputs a light pulse generated on the light source 14 to the light transmission unit 20 connected. The light I/O unit 12 introduces fluorescence to the light pulse transmitted from the light transmission unit 20, and sends it to the detector 15.

The driving unit 13 generates an electric pulse and a synchronization signal for driving the light source 14 and the detector 15, transmits the electric pulse to the light source 14 and transmits the synchronization signal to the detector 15. As a driving system in the driving unit 13, a high output pulse generator can be used. The high output pulse generator generates an electric pulse having a repetition frequency of 1 MHz and a pulse width of 1.5 ns, for example. The electric pulse is applied to, for example, a high output semiconductor laser in the light source 14, and the high output semiconductor laser generates an ultrashort pulse light.

The light source 14 has the above-described high output semiconductor laser (hereinafter referred to as "LD"), for example. In the present application, not only the LD, but also other devices such as a fiber laser and a solid laser can be used. The light source 14 generates the light pulse by, for example, gain switching the LD depending on the electric pulse sent from the driving unit 13, and transmits the light pulse generated to the light I/O unit 12. The light source 14 has at least a function to generate a light pulse having time widths shorter than a fluorescence lifetime of a photosensitizer used. The light pulse (hereinafter called as an "excited light") generated excites the photosensitizer that is matched with the sample (cells) 40 as the object via the light transmission unit 20, and induces a photochemical reaction.

The detector 15 turns on/off a detecting function by the synchronization signal transmitted from the driving unit 13. The detector 15 may be configured to have a shutter to turn on/off inputted light to be detected and to turn on/off the shutter by the synchronization signal. The detector 15 detects fluorescence transmitted from the light I/O unit 12 based on the synchronization signal transmitted from the driving unit 13 at a predetermined timing, and transmits the detected result to the controller 16. In other words, a light generated by the above-described photochemical reaction (called as "fluorescence") is routed via the light transmission unit 20, and is measured at the detector 15. At this moment, by synchronizing a detection timing with the electric pulse applied to the LD in the light source 14, it is possible to gain a time change waveform of the fluorescence.

Figure 3:
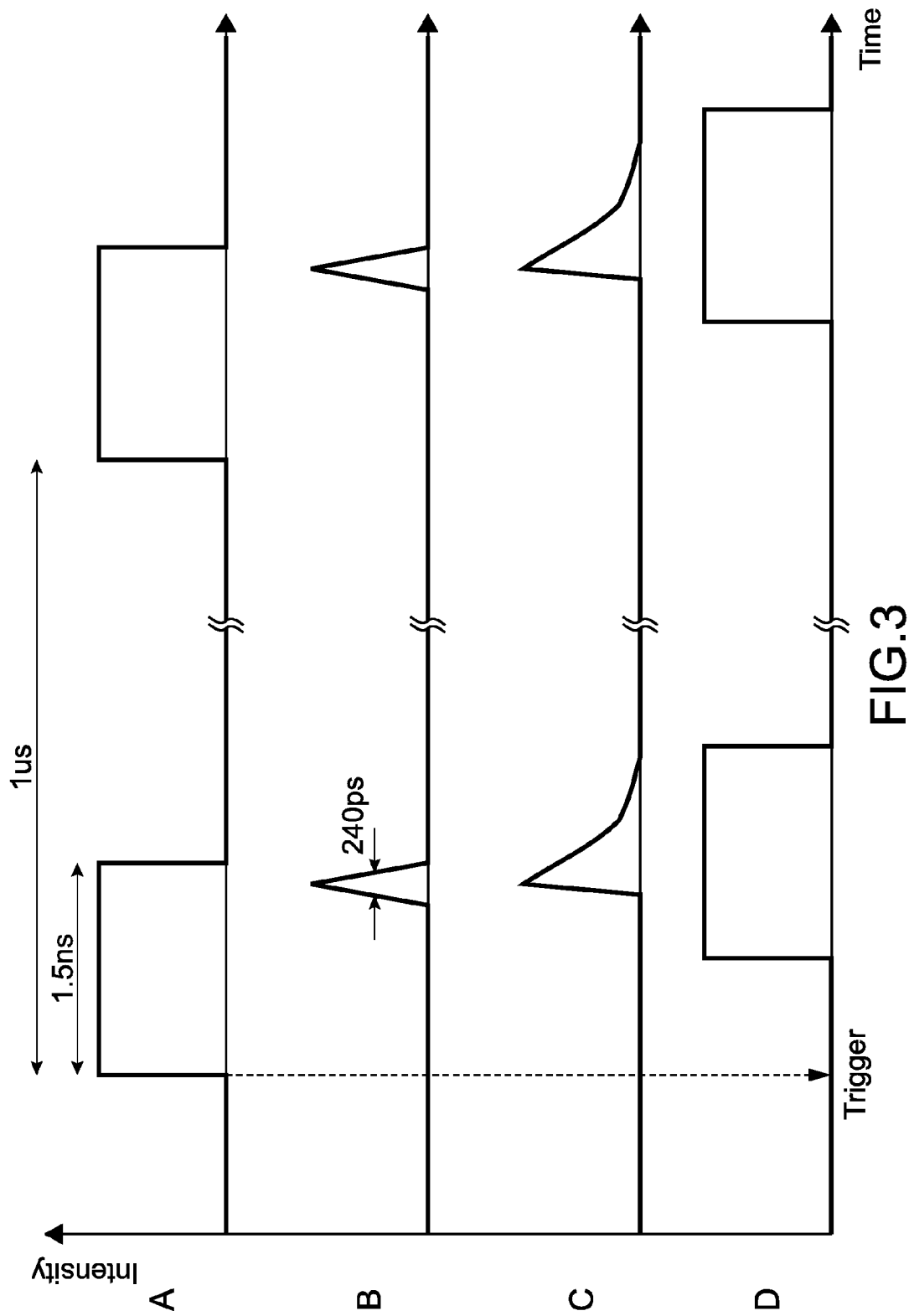
FIG. 3 shows a time chart of the fluorescence measurement according to an embodiment of the present application.

FIG. 3 shows a time chart of the fluorescence measurement. The detector 15 includes a light detector or an image sensor that can measure the time change waveform of the fluorescence at a response speed higher than the fluorescence lifetime of the photosensitizer used. Specific examples of the device include a streak camera, a photomultiplier, a CCD, a CMOS and a photodiode (PD).

In FIG. 3, A shows an electric pulse applied to the LD in the light source 14 by the driving unit 13. The electric pulse has a repetition frequency of 1 MHz (a cycle of 1 μs) and a pulse width of 1.5 ns, for example, as described above. In FIG. 3, B shows a light pulse (of excited light) generated from the LD in the light source 14. The light pulse is triggered by the generation of the electric pulse and is generated at a delay of a predetermined time from electric pulse rise. The light pulse has a pulse width of 240 ps, for example.

In FIG. 3, C shows fluorescence generated from the cells (sample) to the light pulse. The fluorescence starts to emit light at an almost same timing to the light pulse, and finishes to emit light at a slight delay from the light pulse. In FIG. 3, D shows the synchronization signal transmitted from the driving unit 13 to the detector 15. The detector 15 is turned on/off or turns on/off the shutter by the synchronization signal. In D of FIG. 3, a waveform rise represents that the detector 15 is turned on or the shutter in the detector 15 is turned on. In the detector 15, when the image sensor is used as the detection device, "on" in D of FIG. 3 may correspond to an image processing timing.

Desirably, the synchronization signal rises for at least the duration that fluorescence shown in C of FIG. 3 is emitted, or the duration as same as possible. The synchronization signal may be generated at a delay of a predetermined time from the electric pulse shown in A of FIG. 3, for example. When a time interval of the electric pulse rise is longer than the duration that the fluorescence is emitted, the synchronization signal can be used without change by delaying the electric pulse for a predetermined time.

The controller 16 controls actions of the driving unit 13, the light source 14 and the detector 15 depending on the operating instructions inputted from the operation unit 11. The controller 16 performs a predetermined processing based on the fluorescence detected by the detector 15, and outputs a monitor signal to the monitor 30 via connection unit 17.

Figure 4:
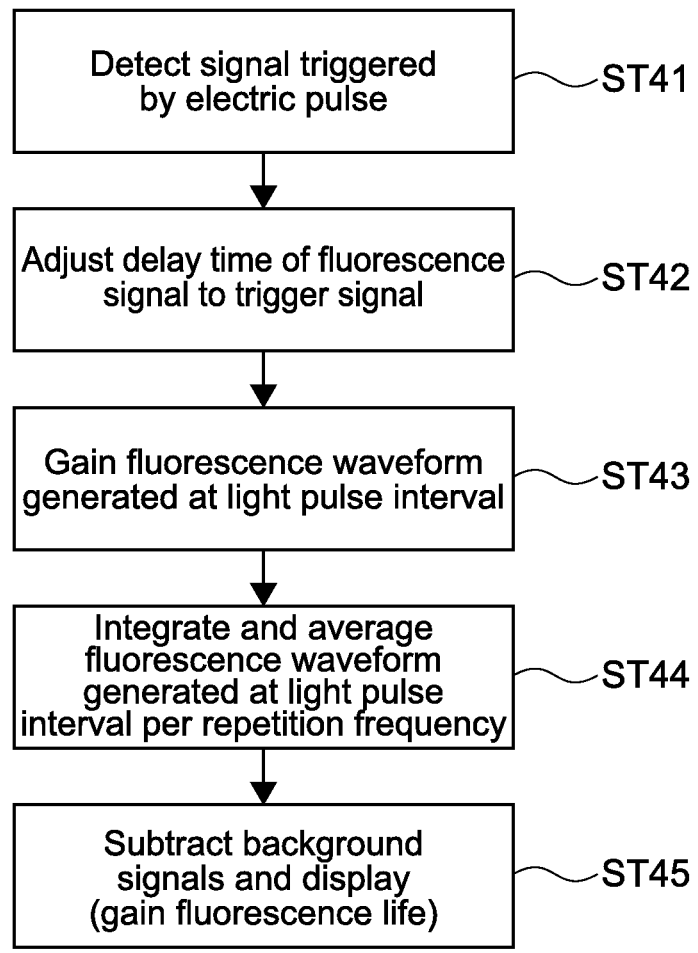
FIG. 4 is a time flow showing an action of fluorescence measurement according to an embodiment of the present application.

FIG. 4 is a time flow showing an action of fluorescence measurement by the controller 16. The controller 16 is configured to run a CPU by software stored in a memory. Other configuration may be taken.

When an operating instruction for fluorescence measurement is inputted, the controller 16 outputs an electric pulse to the driving unit 13, and the light source 14 outputs thereby a light pulse to turn on the detector 15. The controller 16 detects a signal triggered by the electric pulse rise as shown in A of FIG. 3 (step 41), and adjusts the delay time of a fluorescence signal to the triggered signal (step 42). The fluorescence signal is obtained from fluorescence as shown in C of FIG. 3. The controller 16 regard the delay time as the delay time of the synchronization signal shown in D of FIG. 3.

The detector 15 is turned on/off or turns on/off the shutter in the detector 15 by the synchronization signal having the delayed time. In this way, the controller 16 sequentially gains a time change waveform of the fluorescence generated at a light pulse from the detector 15 (step 43). The controller 16 integrates and averages the time change waveform of the fluorescence generated at a light pulse interval per repetition frequency (step 44). The controller 16 gains a fluorescence lifetime by subtracting the background signal from the time change waveform of the fluorescence averaged, and displays the time change waveform of the fluorescence averaged and the fluorescence lifetime on the monitor 30 (step 45).

As the time change waveform of fluorescence to a light pulse is small, it is difficult to calculate the fluorescence lifetime. According to the present application, as the time change waveform of fluorescence integrated per repetition frequency is used, the fluorescence lifetime can be easily calculated.

(Configuration of Light Transmission Unit)

As shown in FIG. 2, the light transmission unit 20 includes a cable 21 having a length of about 1 to 2 m including optical fibers, a connection unit 22 connected to one end of the cable 21, and a main unit 23 connected to other end of the cable 21. The connection unit 22 is connected attachably/detachably to the light I/O unit 12 in the photodynamic diagnosis apparatus main body 10. The light I/O unit 12 may be extended to outside of the photodynamic diagnosis apparatus main body 10 by a cable, and may be connected there attachably/detachably to the connection unit 22.

Figure 5:
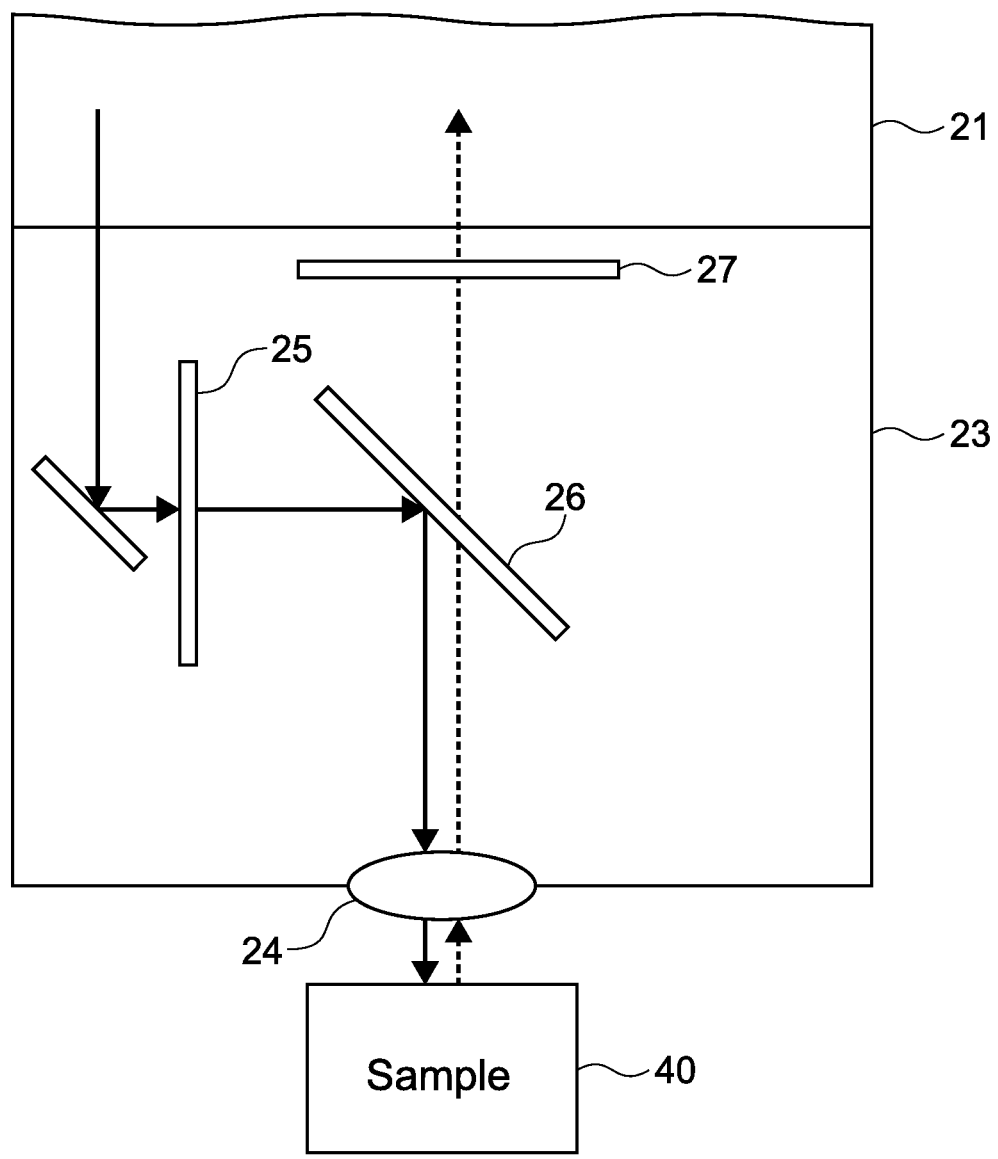
FIG. 5 is a schematic diagram showing the configuration of the main unit of a light transmission unit according to an embodiment of the present application.

FIG. 5 is a schematic diagram showing the configuration of the main unit 23.

Here, a peak wavelength of excited light is $\lambda e$, and a peak wavelength of fluorescence is $\lambda f$. As shown in FIG. 5, the main unit 23 includes a light collecting lens 24 that is an objective lens, a long wavelength cut filter 25 that blocks a wavelength longer than λe, a dichroic mirror 26 that is designed to have high reflectance near λe, and a short wavelength cut filter 27 that blocks a wavelength shorter than λf.

The excited light entered into the main unit 23 from the photodynamic diagnosis apparatus main body 10 passes through the long wavelength cut filter 25. The excited light changes its light path by the dichroic mirror 26, and is exited to a sample 40 via a collecting lens 24. On the other hand, a light (fluorescence) generated from the sample 40 passes through the dichroic mirror 26, and is exited to the photodynamic diagnosis apparatus main body 10 via the short wavelength cut filter 27.

As described above, when the peak wavelength of excited light is λe and the peak wavelength of fluorescence is λf, it is generally known that a relationship may always be λe<λf from an energy level relationship. According to the present application, utilizing this, an optical system of the light transmission unit 20 is configured.

Most of the excited light incident on the main unit 23 is lead to the sample 40 by the dichroic mirror 26 via the light collecting lens 24, and is not lead to the photodynamic diagnosis apparatus main body 10 from the dichroic mirror 26 via the short wavelength cut filter 27. In addition, even if the excited light may be lead to the photodynamic diagnosis apparatus main body 10 via the short wavelength cut filter 27, the excited light is trapped by the short wavelength cut filter 27. On the other hand, the fluorescence from the sample 40 is exited to the photodynamic diagnosis apparatus main body 10 via the dichroic mirror 26 and the short wavelength cut filter 27. The excited light reflected by the sample 40 is double trapped by the dichroic mirror 26 and the short wavelength cut filter 27.

In the light transmission unit 20 having the configuration according to the present application, it is possible to lead only or most of drug fluorescence from a light (including reflection components of the excited light) generated from the sample to the photodynamic diagnosis apparatus main body 10.

(Diagnosis using Photodynamic Diagnosis Apparatus)

Figure 6:
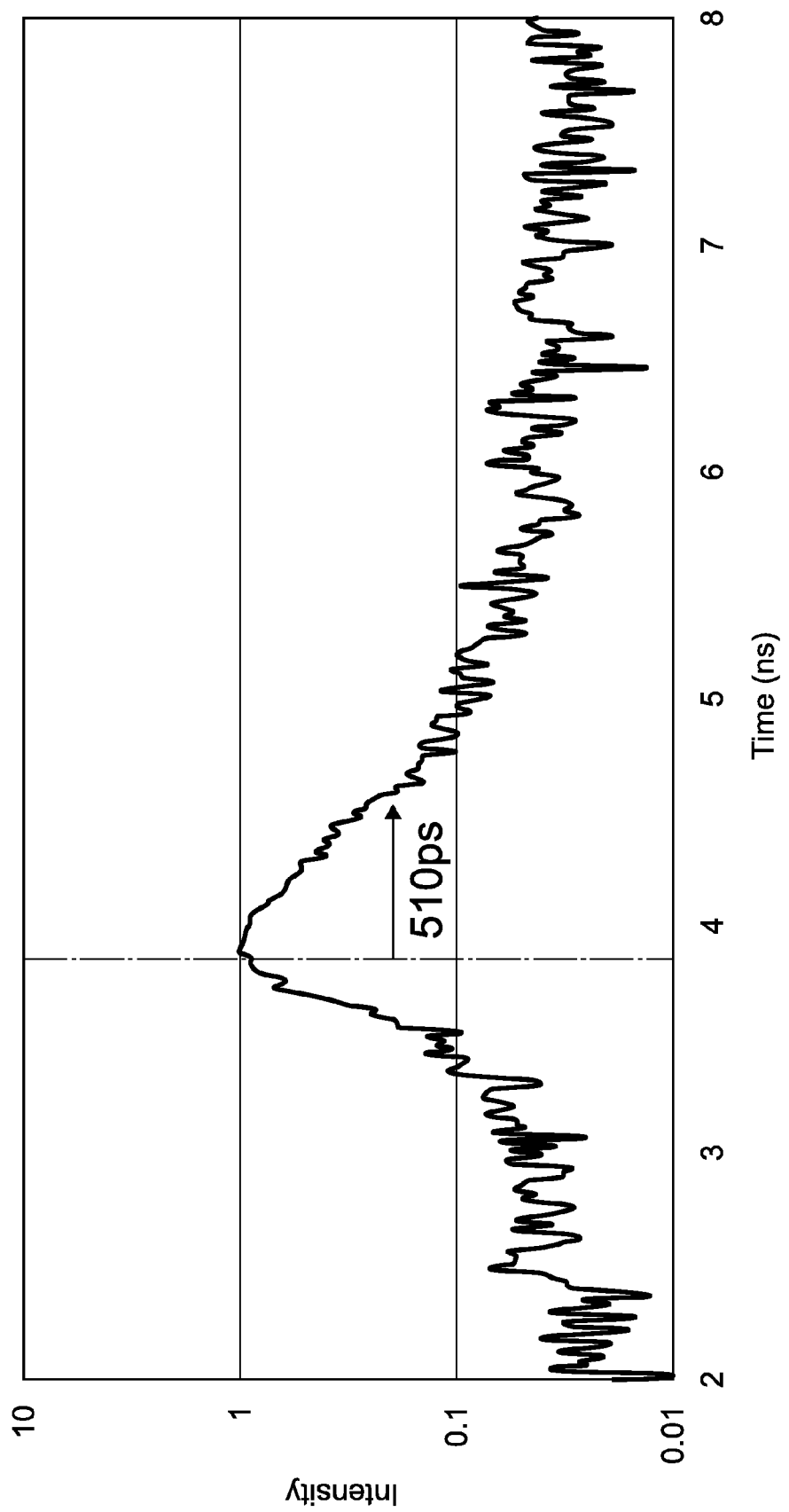
FIG. 6 is a diagram showing a time change waveform of fluorescence measured according to an embodiment of the present application.
Figure 7:
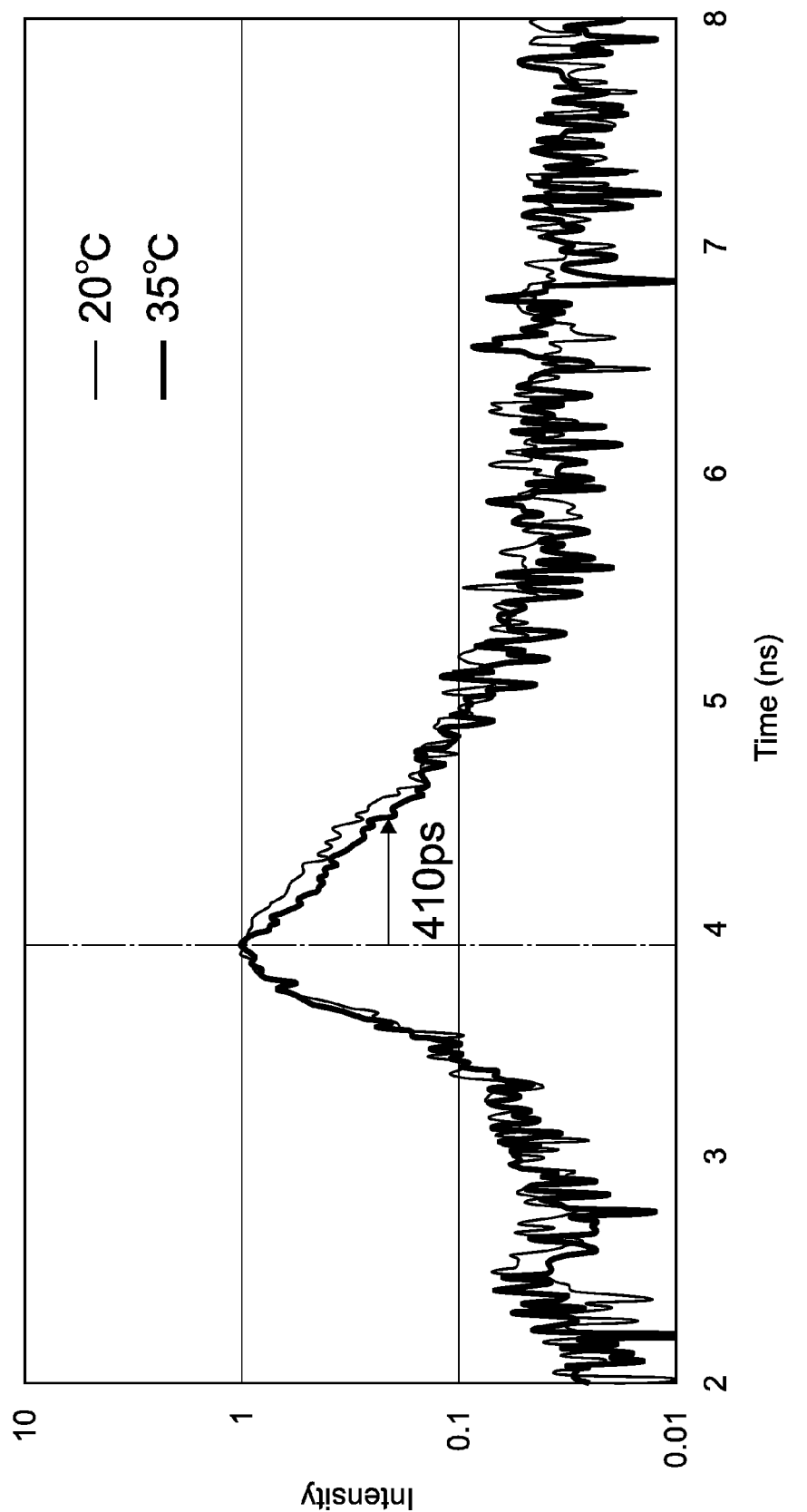
FIG. 7 is a diagram showing a time change waveform of fluorescence measured according to an embodiment of the present application.

FIGS. 6 and 7 show time change waveforms of fluorescence measured using a streak camera (type: C1120) manufactured by Hamamatsu Photonics K.K. at the detector 15. Here, the photosensitizer applied to the sample was methylene blue (tetramethylthionine chloride trihydrate, $C_{16}H_{18}N_3SCl\ 3H_2O$) and was dissolved in a buffer liquid to provide a sample solution. The excited light is a light pulse (a pulse width of 240 ps, a repetition frequency of 1 MHz) generated by gain switching a semiconductor laser. FIG. 6 shows a time change waveform of fluorescence at a sample temperature of 20° C., and FIG. 7 shows a time change waveform of fluorescence at a sample temperature of 35° C.

As shown in FIG. 6, it is found that the fluorescence lifetime (the time taken until a peak intensity of 1/e) of the drug is about 510 ps at the sample temperature of 20° C. In contrast, as shown in FIG. 7, at the sample temperature of 35° C., the fluorescence lifetime of the drug is about 410 ps. Thus, the fluorescence lifetime is shortened.

The fluorescence lifetime differs because an equilibrium velocity constant of the photochemical reaction increases depending on the temperature. In other words, there is correlation between the sample temperature and the fluorescence lifetime. It means that a new diagnosis index may be provided.

Figure 8:
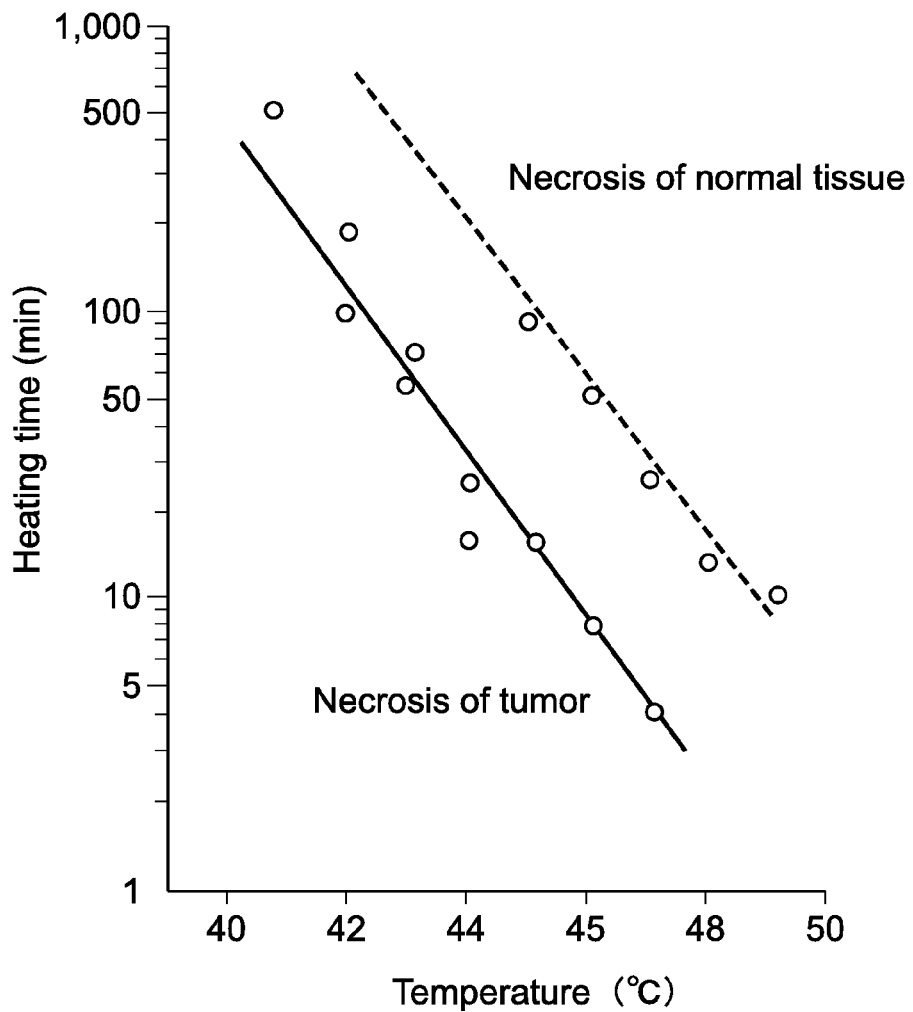
FIG. 8 is a diagram showing a relationship between a temperature for a same hyperthermic effect and a processing time (S-180 tumor) (excerpt from "basic knowledge and safety management of ME" p.329 (FIG. 26-2), supervised by Japanese Society for ME (Medical and Biological Engineering), ME Technician Education Council, Nankodo, Co., Ltd.)

For example, as shown in FIG. 8, it is found that heat tolerance (characteristics to temperature) is different in a normal cell and a tumor cell. By utilizing this, the time change waveform of the fluorescence is analyzed, thereby providing the diagnosis index about tumor progression.

In the diagnosis using the photodynamic diagnosis apparatus 1, the fluorescence lifetime may be measured by the operator. For example, the fluorescence lifetime may be displayed by calculating the time taken until the peak intensity becomes 1/e at the photodynamic diagnosis apparatus 1. Also, a tumor staging may be quantified based on the fluorescence lifetime calculated on the photodynamic diagnosis apparatus 1.

Figure 9:
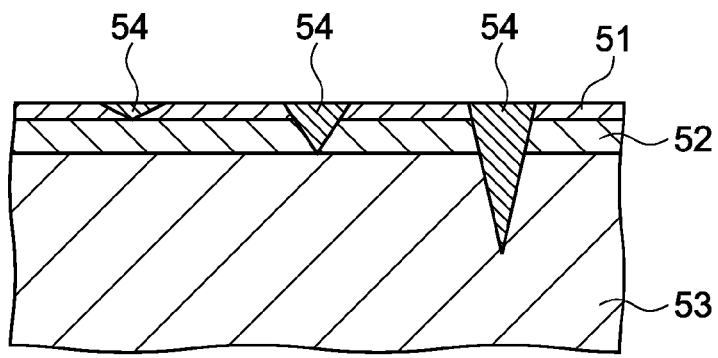
FIG. 9 shows a conceptual diagram showing an invasion of a malignant tumor from a surface of a large intestine.

FIG. 9 shows a conceptual diagram showing an invasion of a malignant tumor from a surface of a large intestine.

As shown in FIG. 9, the surface of the large intestine is overlapped with a mucous membrane 51. There is a submucous membrane 52 thereunder, and a muscularis propria 53 thereunder.

In FIG. 9, areas 54 defined by dashed lines each represents a malignant tumor. In general, as the time is elapsed, the malignant tumor 54 is invaded from the surface of the large intestine in the order of the left area, the middle area and the right area. In the left area, the malignant tumor 54 is invaded only to a mucous membrane 51. In the middle area, the malignant tumor 54 is invaded to a submucous membrane 52. In the right area, the malignant tumor 54 is invaded to a muscularis propria 53.

Figure 10:
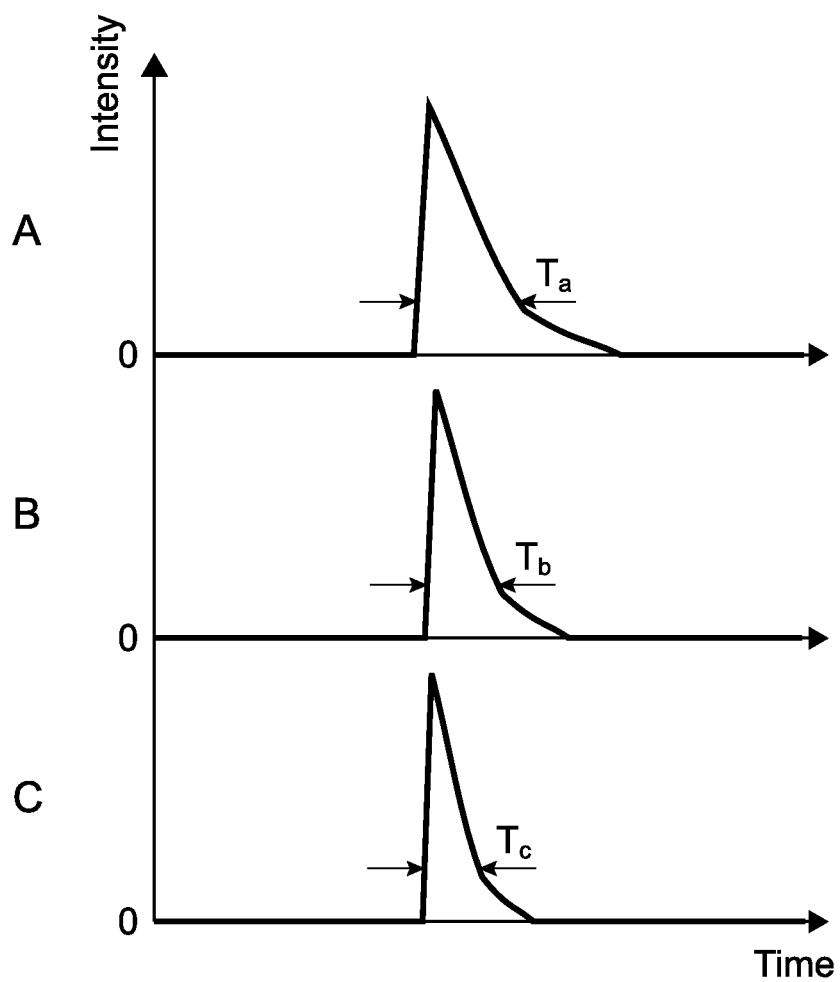
FIG. 10 shows a relationship between invasion of a large intestine cancer and the fluorescence lifetime according to an embodiment of the present application.

FIG. 10 shows a relationship between invasion of a large intestine cancer and the fluorescence lifetime.

In FIG. 10, A represents the fluorescence lifetime when the malignant tumor 54 is invaded only to the mucous membrane 51. The fluorescence lifetime in this case is referred to as Ta. B represents the fluorescence lifetime when the malignant tumor 54 is invaded to the submucous membrane 52. The fluorescence lifetime in this case is referred to as Tb. C represents the fluorescence lifetime when the malignant tumor 54 is invaded to the muscularis propria 53. The fluorescence lifetime in this case is referred to as Tc.

When these fluorescence lifetimes are compared, it is found that Ta>Tb>Tc.

In other words, it is found that the fluorescence lifetime is shorter depending on an invasion degree of the tumor. It also means that a new diagnostic index can be provided. In the determination of the large intestine cancer, a surgical approach can be selected depending on the layer to which the cancer is invaded, thereby very beneficial diagnostic index is provided.

Therefore, in the diagnosis using the photodynamic diagnosis apparatus 1, when the operator measures the fluorescence lifetime, the invasion degree of the tumor can be diagnosed, for example. As another example, the fluorescence lifetime may be calculated and displayed at the photodynamic diagnosis apparatus 1. As still another example, the invasion degree of the tumor may be quantified and displayed based on the fluorescence lifetime calculated at the photodynamic diagnosis apparatus 1.

Japanese Patent Application Laid-open No. 2011-218149 discloses a technology that an acoustic wave generated from a sample matched to a drug is measured using a pulse laser and is utilized for diagnosis. Japanese Patent Application Laid-open No. 2008-43383 discloses a technology that a light source is multiwaved to increase the resultant fluorescence images, which are used for diagnosis. The entire contents of these technologies disclosed are incorporated into the present specification. However, the photodynamic diagnosis apparatus 1 is essentially different from the technologies disclosed above in that the photodynamic diagnosis apparatus 1 includes the light source 14 capable of generating a light pulse having a time width shorter than the fluorescence lifetime of the photosensitizer, and the detector 15 capable of measuring a time change waveform of the fluorescence to the light pulse. In other words, the present application focuses on the time change waveform of the fluorescence in the photosensitizer, measures the time change waveform of the fluorescence to determine the fluorescence lifetime by the above-described configurations, and provides a new diagnosis index from the fluorescence lifetime.

(Other Configuration of Photodynamic Diagnosis Apparatus)

Figure 11:
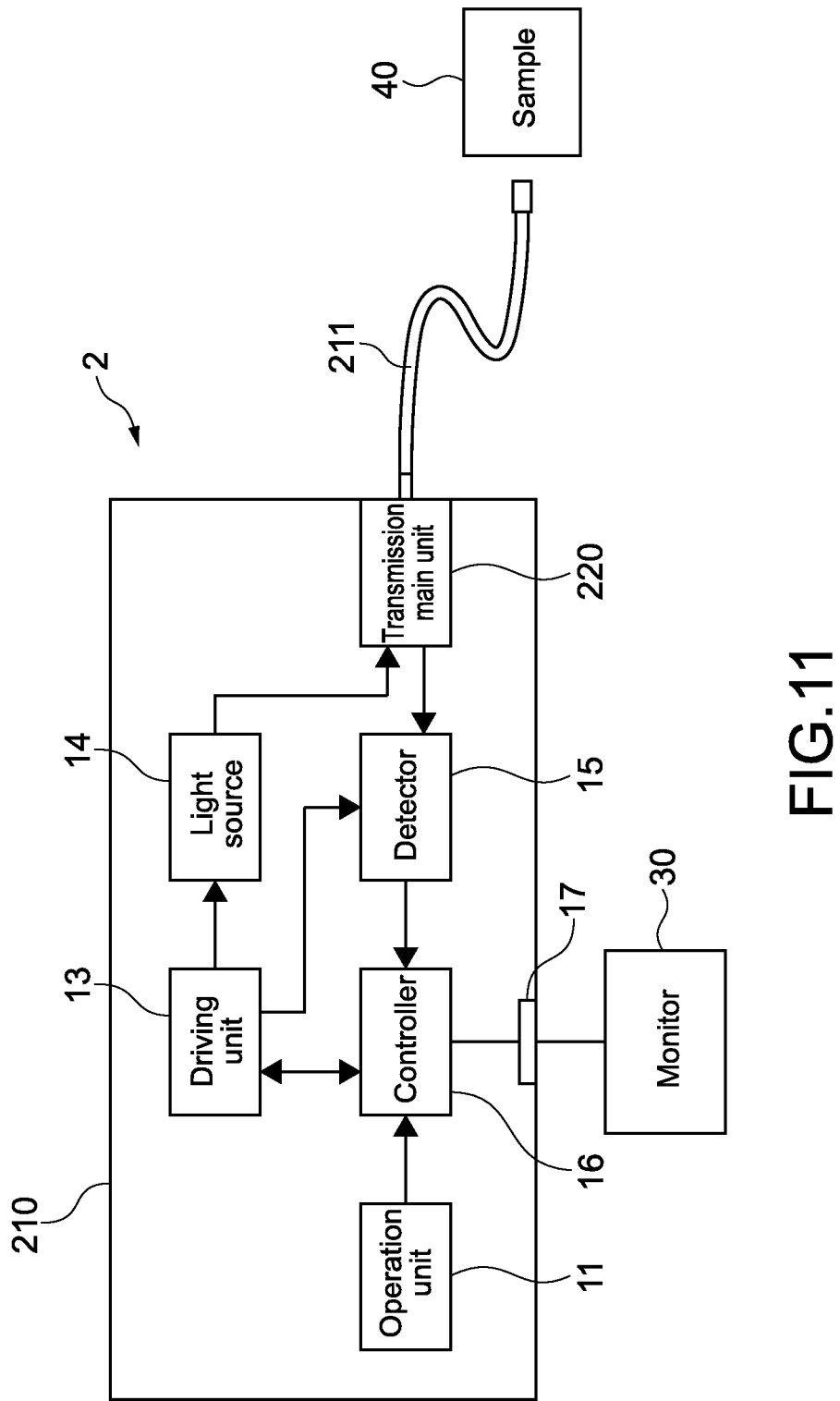
FIG. 11 is a block diagram showing a configuration of a photodynamic diagnosis apparatus according to other embodiment of the present application.

FIG. 11 is a block diagram showing other configuration of the photodynamic diagnosis apparatus according to the present application. In FIG. 11, to indicate that it is the same configuration, as appropriate, the configuration denoted by the same symbols in FIGS. 1 and 2, and descriptions thereof will be omitted.

As shown in FIG. 11, a photodynamic diagnosis apparatus 2 includes a photodynamic diagnosis apparatus main body 210, a cable unit 211 and a monitor 30. The photodynamic diagnosis apparatus main body 210 includes the operation unit 11, a light transmission main unit 220, the driving unit 13, the light source 14, the detector 15, the controller 16 and the monitor connection unit 17. In a photodynamic diagnosis apparatus main body 210 shown in FIG. 11, the constituents of the light transmission main unit 220 are different from those of the photodynamic diagnosis apparatus 1 as shown in FIGS. 1 and 2.

Figure 12:
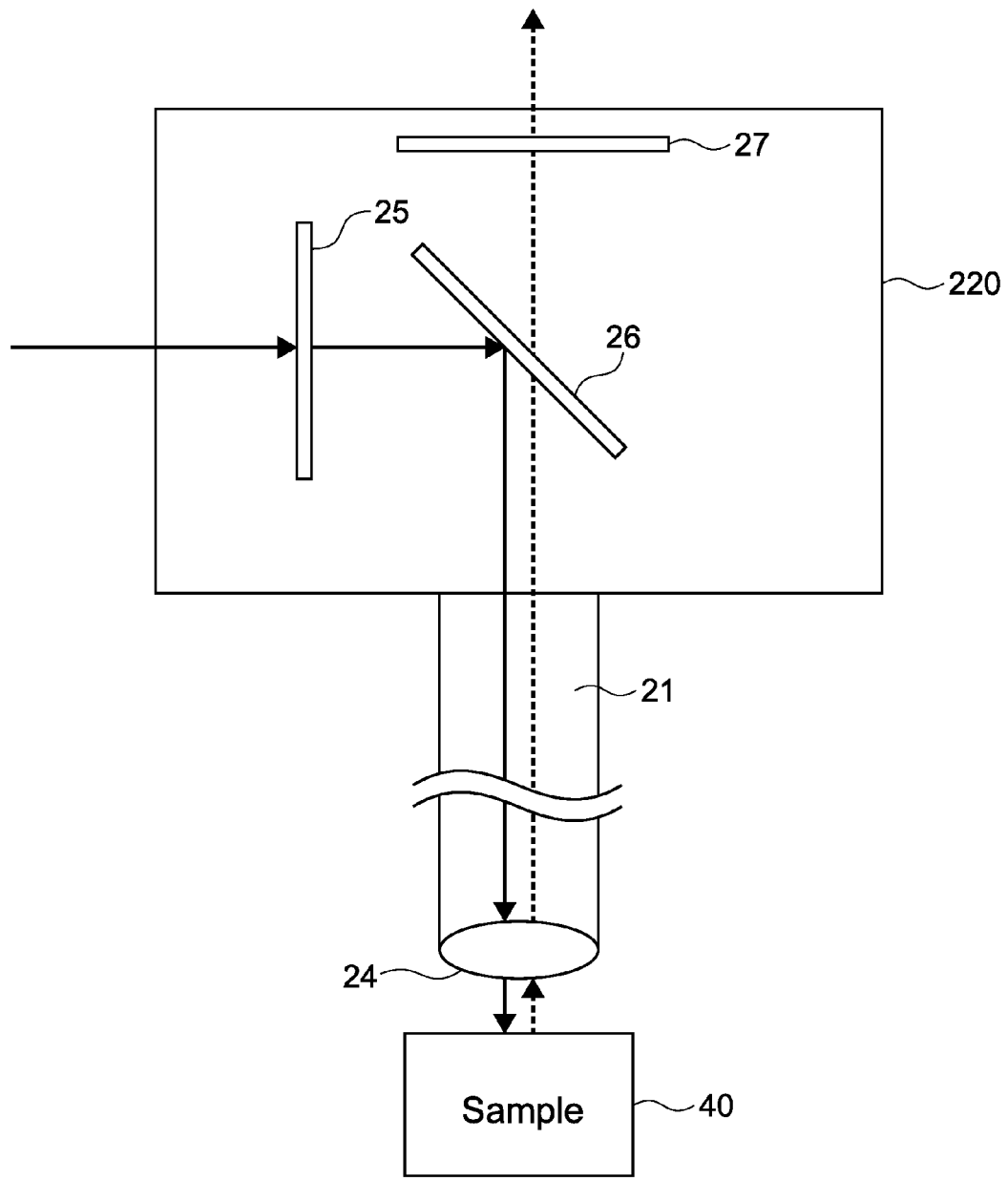
FIG. 12 is a block diagram showing the configuration of the light transmission main unit shown in FIG. 11.

The light transmission main unit 220 includes a long wavelength cut filter 25, the dichroic mirror 26 and the short wavelength cut filter 27, as shown in FIG. 12. In the cable unit 211, a collective lens 24 is attached to one end of the cable 21 having a length of about 1 to 2 m including the optical fibers, and the light transmission main unit 220 of the photodynamic diagnosis apparatus main body 210 is connected attachably/detachably to other end of the cable 21.

The photodynamic diagnosis apparatus 2 having the above-described configuration is different from the photodynamic diagnosis apparatus 1 shown in FIGS. 1 and 2 in that the light transmission main unit 220 is included within the photodynamic diagnosis apparatus main body 210.

(Other Photodynamic Diagnosis Apparatus)

The photodynamic diagnosis apparatus according to the present application can be applied to other devices such as an endoscope and a laser microscope.

Figure 13:
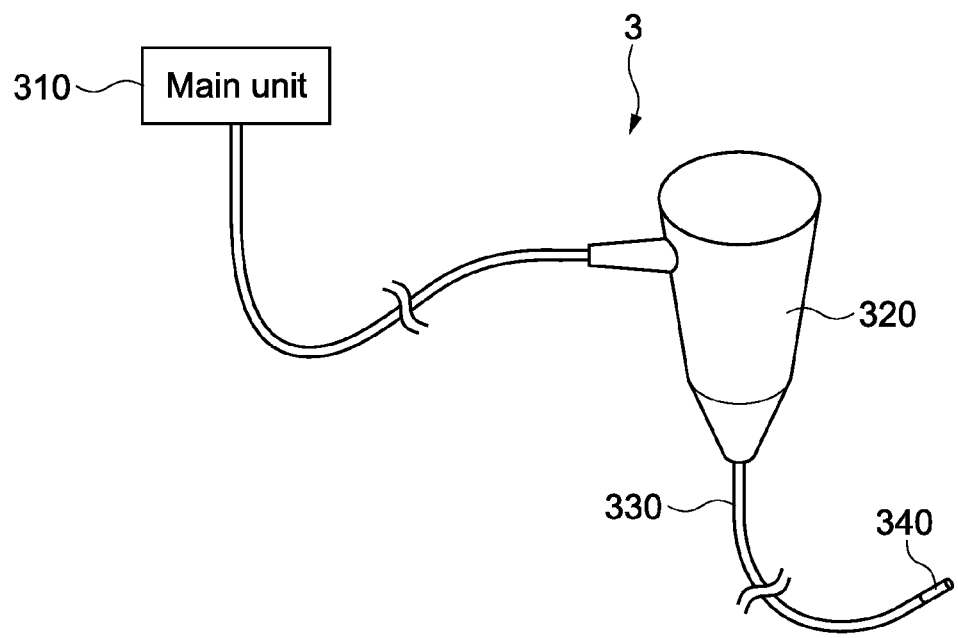
FIG. 13 shows a configuration of an endoscope according to the present application.

FIG. 13 shows a configuration of an endoscope having a function as the photodynamic diagnosis apparatus according to the present application.

As shown in FIG. 13, an endoscope 3 includes a main unit 310, an operation unit 320, an insertion unit 330 and a tip 340.

The main unit 310 includes a supply unit for supplying the tip 340 with light and air, an image processing unit for processing images from the tip 340, a photodynamic diagnosis unit (any of them are not shown) or the like.

The photodynamic diagnosis unit in the main unit 310 has a configuration of the photodynamic diagnosis apparatus main body 10 shown in FIG. 2. In other words, the photodynamic diagnosis unit in the main unit 310 includes the operation unit 11, the light input/output (I/O) unit 12, the driving unit 13, the light source 14, the detector 15, the controller 16 and the monitor connection unit 17, as shown in FIG. 2. Image data from the image processing unit in the main unit 310 is outputted to the monitor 30 via the monitor connection unit 17 (see FIG. 2). In the monitor 30, the image captured by the endoscope 3 is displayed.

By the operation unit 320, the operator operates the endoscope 3. By the operation unit 320, the endoscope 3 is angled, air is sucked, air is supplied, water is fed and forceps is inserted.

The insertion unit 330 is inserted into a captured site.

Figure 14:
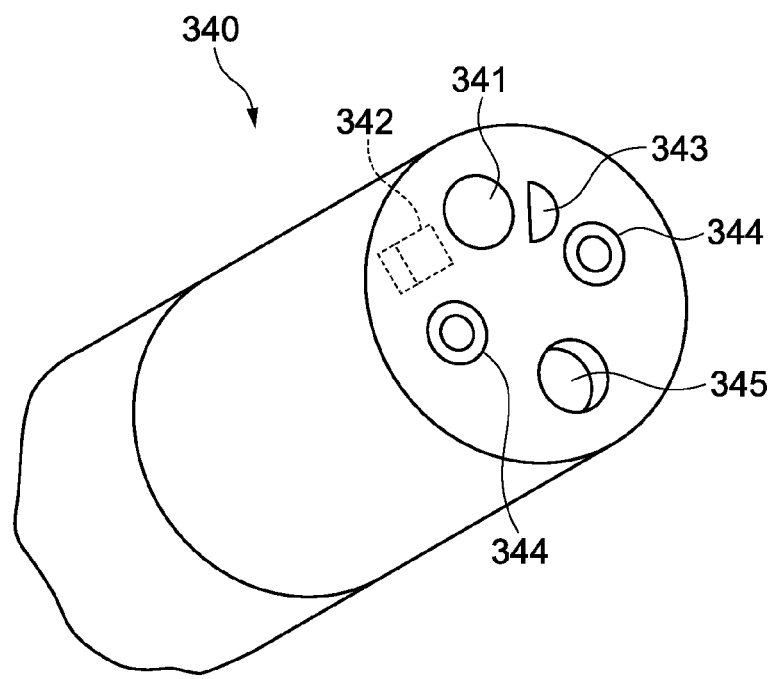
FIG. 14 shows the configuration of a tip in the endoscope shown in FIG. 13.

As shown in FIG. 14, the tip 340 includes an objective lens 341, a capturing unit 342 such as a CCD image sensor, a nozzle 343 for feeding water or air, light guides 344 for illuminating the captured site, and a forceps slot 345 for collecting tissues, in addition to the configuration of the light transmission unit 20 shown in FIG. 5.

The endoscope 3 thus configured not only has a function as the endoscope, but also can perform the photodynamic diagnosis as shown in the first embodiment.

Next, the embodiment where the present application is applied to the laser microscope will be described.

Figure 15:
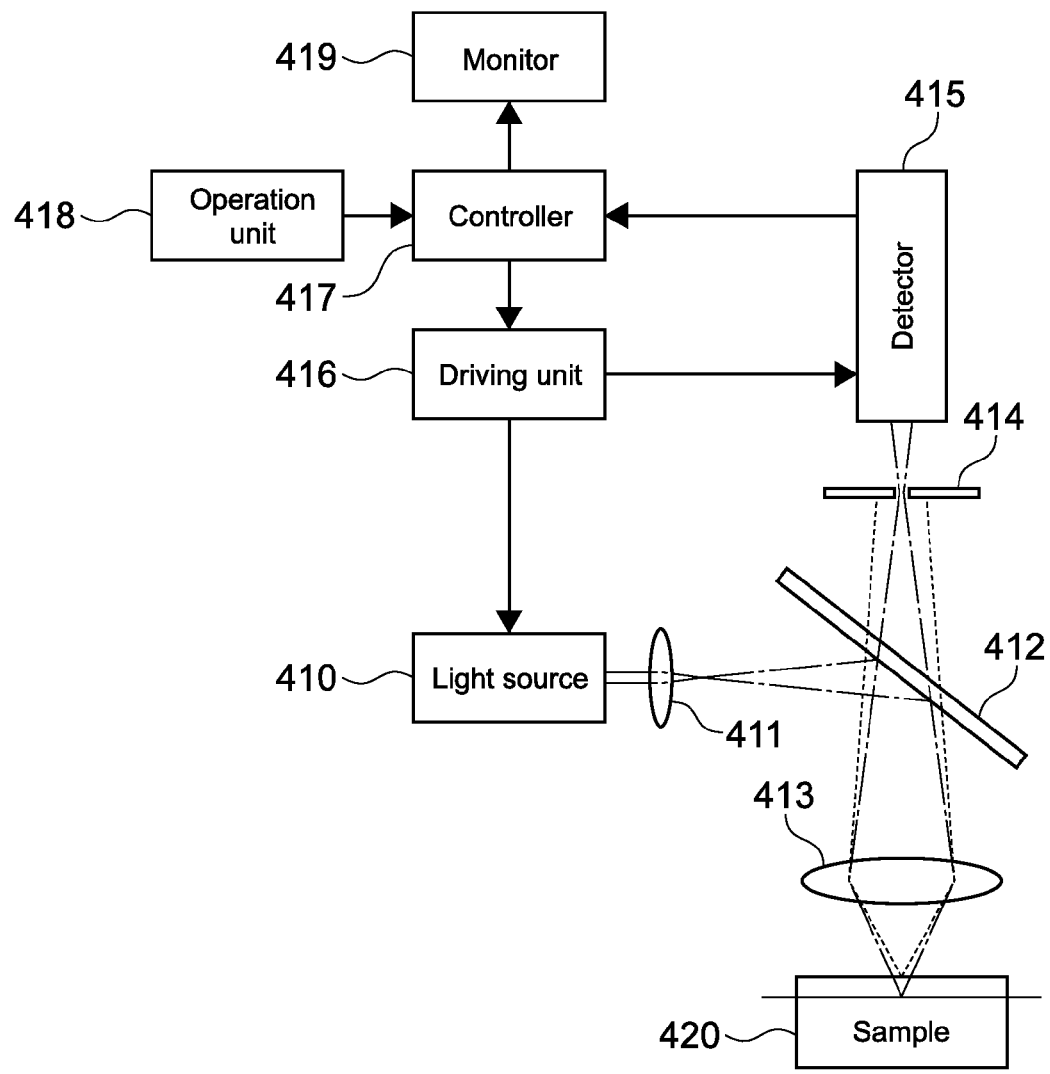
FIG. 15 shows a configuration of a laser microscope according to the present application.

FIG. 15 shows a configuration of a laser microscope having a function as the photodynamic diagnosis apparatus according to the present application.

As shown in FIG. 15, a laser microscope 4 includes a light source 410, a lens 411, a dichroic mirror 412, an objective lens 413, a pin hole 414, a detector 415, a driving unit 416, a controller 417, an operation unit 418 and a monitor 419.

The light source 410, the detector 415, the driving unit 416, the controller 417 and the operation unit 418 may have the configurations similar to the aforementioned embodiment.

The light pulse generated from the light source 410 passes through the lens 411, the dichroic mirror 412 and the objective lens 413, excites the photosensitizer that is matched with a sample (cells) 420 as the object, and induces a photochemical reaction. The fluorescence generated by the photochemical reaction passes through the objective lens 413, the dichroic mirror 412 and the pin hole 414, and is measured at the detector 415. At the detector 415, the time change waveform of the fluorescence is gained. By the time change waveform, the fluorescence lifetime of the sample 420 is detected. Thus, there can be provided a new diagnosis index about the tumor staging and the invasion degree in the depth direction of the tumor.

In the laser microscope shown in FIG. 15, the long wavelength cut filter may be disposed between the light source 410 and the dichroic mirror 412, and the short wavelength cut filter may be disposed between the dichroic mirror 412 and the detector 415.

(Other)

The present application is not limited to the above-described embodiments, and may be implemented in various other embodiments.

The present application may have the following configurations.

(1) A photodynamic diagnosis apparatus, including:
a light source for generating a light pulse having a time width shorter than a fluorescence lifetime of a photosensitizer; and
a detector for measuring a time change waveform of the fluorescence to the light pulse.

(2) The photodynamic diagnosis apparatus according to (1) above, further including:
a controller for sequentially gaining the time change waveform of the fluorescence generated by the light pulse generated at the light source from the detector, integrating and averaging a plurality of the waveforms per repetition frequency, and gaining the fluorescence lifetime by subtracting a background signal from the waveform averaged.

(3) The photodynamic diagnosis apparatus according to (1) or (2) above, in which
the detector includes a device for measuring the time change waveform of the fluorescence to the light pulse at a response speed higher than the fluorescence lifetime of the photosensitizer.

(4) The photodynamic diagnosis apparatus according to (3) above, in which
the device is one selected from a streak camera, a photomultiplier, a CCD, a CMOS and a photodiode.

(5) The photodynamic diagnosis apparatus according to any one of (1) to (4) above, further including:
a driving unit for generating a synchronization signal that is synchronized with an electric pulse for driving the light source and an electric pulse for driving the detector and is delayed by the electric pulse, in which
the light source generates the light pulse based on the electric pulse, and
the detector controls a light receiving duration of the fluorescence based on the synchronization signal.

(6) The photodynamic diagnosis apparatus according to any one of (1) to (5) above, further including:
a dichroic mirror having high reflectance near a peak wavelength of the light pulse that reflects the light pulse from the light source, directs the light pulse to an object and transmits the fluorescence from the object;
a long wavelength cut filter disposed at a light path between the light source and the dichroic mirror that blocks a wavelength longer than a peak wavelength of the light pulse; and
a short wavelength cut filter disposed at a light path between the dichroic mirror and the detector that blocks a wavelength shorter than a peak wavelength of the photosensitizer.

(7) A photodynamic diagnosis method, including:
generating a light pulse having a time width shorter than a fluorescence lifetime of a photosensitizer;
irradiating an object with the light pulse generated; and
measuring a time change waveform of fluorescence to the light pulse generated from the object.

(8) The photodynamic diagnosis method according to (7) above, in which
a fluorescence lifetime is determined based on the time change waveform of the fluorescence, and
a diagnosis index about the tumor staging is gained based on the fluorescence lifetime.

(9) The photodynamic diagnosis method according to (7) or (8) above, in which
a fluorescence lifetime is determined based on the time change waveform of fluorescence, and
a diagnosis index about an invasion degree of a tumor is gained based on the fluorescence lifetime.

(10) The photodynamic diagnosis method according to any one of (7) to (9) above, further including:
sequentially gaining the time change waveform of the fluorescence generated by the light pulse;
integrating and averaging a plurality of the waveforms per repetition frequency; and
gaining the fluorescence lifetime by subtracting a background signal from the waveform averaged.

(11) A attachable/detachable device to a photodynamic diagnosis apparatus main body including a light source for generating a light pulse having a time width shorter than a fluorescence lifetime of a photosensitizer, and a detector for measuring a time change waveform of the fluorescence to the light pulse, including:
a cable for transmitting a light pulse generated by the light source, irradiating an object with the light pulse, inputting fluorescence to the light pulse irradiated, and transmitting the fluorescence to the detector;
a dichroic mirror having high reflectance near a peak wavelength of the light pulse that reflects the light pulse from the light source, directs the light pulse to an object and transmits the fluorescence from the object;
a long wavelength cut filter disposed at a light path between the light source and the dichroic mirror that blocks a wavelength longer than a peak wavelength of the light pulse; and
a short wavelength cut filter disposed at a light path between the dichroic mirror and the detector that blocks a wavelength shorter than a peak wavelength of the photosensitizer.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A photodynamic diagnosis apparatus, comprising:
a light source for generating a light pulse having a time width shorter than a fluorescence lifetime of a photosensitizer; and
a detector for measuring a fluorescence generated when the light pulse excites the photosensitizer,
wherein the detector is configured to measure a time change waveform of the fluorescence to the light pulse,
wherein a plurality of the time change waveforms are integrated and averaged per repetition frequency, and
wherein a diagnosis index about at least one of a tumor staging or an invasion degree is provided based on the integrated time change waveforms of the fluorescence to the light pulse measured by the detector.

2. The photodynamic diagnosis apparatus according to claim 1, further comprising:
a controller for sequentially gaining the time change waveform of the fluorescence generated by the light pulse generated at the light source from the detector, integrating and averaging a plurality of the waveforms per repetition frequency, and gaining the fluorescence lifetime by subtracting a background signal from the waveform averaged.

3. The photodynamic diagnosis apparatus according to claim 1, wherein
the detector includes a device for measuring the time change waveform of the fluorescence to the light pulse at a response speed higher than the fluorescence lifetime of the photosensitizer.

4. The photodynamic diagnosis apparatus according to claim 3, wherein
the device is selected from the group consisting of: a streak camera, a photomultiplier, a CCD, a CMOS and a photodiode.

5. The photodynamic diagnosis apparatus according to claim 1, further comprising:
a driving unit for generating a synchronization signal wherein:

the synchronized signal is synchronized with an electric pulse for driving the light source and is delayed by the electric pulse, the light source generates the light pulse based on the electric pulse, and the detector controls a light receiving duration of the fluorescence based on the synchronization signal.

6. The photodynamic diagnosis apparatus according to claim 1, further comprising:

a dichroic mirror having high reflectance near a peak wavelength of the light pulse that reflects the light pulse from the light source, directs the light pulse to an object and transmits the fluorescence from the object;

a long wavelength cut filter disposed at a light path between the light source and the dichroic mirror that blocks a wavelength longer than a peak wavelength of the light pulse; and a short wavelength cut filter disposed at a light path between the dichroic mirror and the detector that blocks a wavelength shorter than a peak wavelength of the photosensitizer.

7. The photodynamic diagnosis apparatus according to claim 1, wherein the detector is configured to measure the time change waveform of the fluorescence to the light pulse based on a synchronization signal.

8. The photodynamic diagnosis apparatus according to claim 1, wherein the detector is configured to measure the time change waveform of the fluorescence to the light pulse by synchronizing a detection timing with an electric pulse for driving the light source.

9. The photodynamic diagnosis apparatus according to claim 1, wherein the detector is configured to turn a detection function on and off by the synchronization signal.

10. The photodynamic diagnosis apparatus according to claim 1, wherein a second fluorescence lifetime is determined based on the time change waveform of the fluorescence to the light pulse, and the diagnosis index is provided based on the second fluorescence lifetime.

11. A photodynamic diagnosis method, comprising:

generating a light pulse having a time width shorter than a fluorescence lifetime of a photosensitizer;

irradiating an object including the photosensitizer with the light pulse generated to generate a fluorescence when the light pulse excites the photosensitier;

measuring a time change waveform of fluorescence to the light pulse generated from the object;

integrating and averaging a plurality of the time change waveforms of the fluorescence per repetition frequency and determining a diagnosis index about at least one of tumor staging and an invasion degree of a tumor based on the integrated time change waveforms, of the fluorescence to the light pulse.

12. The photodynamic diagnosis method according to claim 11, further comprising:

sequentially gaining the time change waveform of the fluorescence generated by the light pulse; and determining the fluorescence lifetime by subtracting a background signal from the waveform averaged.

13. The photodynamic diagnosis method according to claim 11, further comprising:

determining a fluorescence lifetime based on the time change waveform of the fluorescence, wherein the diagnosis index is determined based on the fluorescence lifetime.

14. A attachable/detachable device to a photodynamic diagnosis apparatus main body including a light source for generating a light pulse having a time width shorter than a fluorescence lifetime of a photosensitizer, and a detector for measuring a fluorescence generated when the light pulse excites the photosensitizer, comprising;

a cable for transmitting a light pulse generated by the light source, irradiating an object with the light pulse, inputting fluorescence to the light pulse irradiated, and transmitting the fluorescence to the detector;

a dichroic mirror having high reflectance near a peak wavelength of the light pulse that reflects the light pulse from the light source, directs the light pulse to an object and transmits the fluorescence from the object;

a long wavelength cut filter disposed at a light path between the light source and the dichroic mirror that blocks a wavelength longer than a peak wavelength of the light pulse; and a short wavelength cut filter disposed at a light path between the dichroic mirror and the detector that blocks a wavelength shorter than a peak wavelength of the photosensitizer, wherein the detector is configured to measure a time change waveform of the fluorescence to the light pulse, wherein a plurality of the time change waveforms are integrated and averaged per repetition frequency, and wherein a diagnosis index about at least one of a tumor staging or an invasion degree is provided based on the integrated time change waveforms of the fluorescence to the light pulse measured by the detector.

15. The attachable/detachable device according to claim 14, wherein a second fluorescence lifetime is determined based on the time change waveform of the fluorescence to the light pulse, and the diagnosis index is provided based on the second fluorescence lifetime.

* * * * *